US011615561B2

(12) United States Patent
Vincelette et al.

(10) Patent No.: US 11,615,561 B2
(45) Date of Patent: Mar. 28, 2023

(54) SYSTEM AND METHOD FOR ACQUIRING AND DISPLAYING AN IMAGE OF A SUBJECT

(71) Applicant: Medtronic Navigation, Inc., Louisville, CO (US)

(72) Inventors: Rebecca L. Vincelette, Arvada, CO (US); Erez Shani, Boulder, CO (US); Christine R. Drown, Westminster, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 50 days.

(21) Appl. No.: 17/080,407

(22) Filed: Oct. 26, 2020

(65) Prior Publication Data

US 2022/0130083 A1 Apr. 28, 2022

(51) Int. Cl.
| | | |
|---|---|---|
| *G06T 11/00* | (2006.01) | |
| *G06T 7/11* | (2017.01) | |
| *G06T 7/73* | (2017.01) | |
| *G16H 30/40* | (2018.01) | |
| *G06T 7/00* | (2017.01) | |

(52) U.S. Cl.
CPC ........ *G06T 11/008* (2013.01); *G06T 7/0012* (2013.01); *G06T 7/11* (2017.01); *G06T 7/73* (2017.01); *G06T 11/001* (2013.01); *G16H 30/40* (2018.01); *G06T 2207/10024* (2013.01); *G06T 2207/10088* (2013.01)

(58) Field of Classification Search
CPC ........ G06T 11/008; G06T 11/001; G06T 7/11; G06T 7/73; G06T 7/0012; G06T 2207/10024; G06T 2207/10088; G16H 30/40
See application file for complete search history.

(56) References Cited

U.S. PATENT DOCUMENTS

| | | | |
|---|---|---|---|
| 8,238,631 B2 | 8/2012 | Hartmann et al. | |
| 2010/0045580 A1* | 2/2010 | Ichikawa | G06T 3/4007 345/87 |
| 2010/0290690 A1 | 11/2010 | Hartmann et al. | |
| 2012/0097178 A1 | 4/2012 | Helm et al. | |
| 2012/0099768 A1 | 4/2012 | Helm et al. | |
| 2012/0099772 A1 | 4/2012 | Helm et al. | |
| 2012/0250822 A1 | 10/2012 | Helm et al. | |

OTHER PUBLICATIONS

Mertens et al. "A sub-pixel mapping algorithm based on sub-pixel/pixel spatial attraction models", International Journal of Remote Sensing, GB, vol. 27, No. 15, Jan. 1, 2006, pp. 3293-3310 (Year: 2006).*

(Continued)

*Primary Examiner* — Vu Le
*Assistant Examiner* — Julius Chai
(74) *Attorney, Agent, or Firm* — Harness, Dickey & Pierce, P.L.C.

(57) ABSTRACT

A method and system is disclosed for displaying acquired image data of a subject. The image may include a high resolution of clear image based on the acquired image data. The image may assist in evaluating the subject.

13 Claims, 6 Drawing Sheets

(56) References Cited

OTHER PUBLICATIONS

P. Wang, L. Wang, H. Leung and G. Zhang, "Super-Resolution Mapping Based on Spatial-Spectral Correlation for Spectral Imagery," in IEEE Transactions on Geoscience and Remote Sensing, vol. 59, No. 3, pp. 2256-2268, Mar. 2021, doi: 10.1109/TGRS.2020. 3004353. (Year: 2020).*
Lu et al., "A New Spatial Attraction Model for Improving Subpixel Land Cover Classification", Remote Sensing 2017, 9, 360, Apr. 2017 (Year: 2017).*
Wang et al., "Integration of spatial attractions between and within pixels for sub-pixel mapping", Journal of Systems Engineering and Electronics, vol. 23, No. 2, Apr. 2012 (Year: 2012).*
B. Denis de Senneville, S. Hey, C. T. W. Moonen and M. Ries, "Super-resolution for real-time volumetric MR-temperature monitoring," 2011 IEEE International Symposium on Biomedical Imaging: From Nano to Macro, 2011, pp. 1684-1687, doi: 10.1109/ISBI. 2011.5872728. (Year: 2011).*
Wang et al., "Sub-pixel mapping of remote sensing images based on radial basis function interpolation", ISPRS Journal of Photogrammetry and Remote Sensing, 92, 2014. (Year: 2014).*
Kim et al., "Accurate Image Super-Resolution Using Very Deep Convolutional Networks", Proceedings of the IEEE conference on computer vision and pattern recognition, 2016. (Year: 2016).*
Shi et al, "Real-time single image and video super-resolution using an efficient sub-pixel convolutional neural network", Proceedings of the IEEE conference on computer vision and pattern recognition, 2016. (Year: 2016).*
Ge et al., "Development and Testing of a Subpixel Mapping Algorithm" IEEE Transactions on Geoscience and Remote Sensing, vol. 47, No. 7, Jul. 2009. (Year: 2009).*
Mahmood et al., "Contextual Subpixel Mapping of Hyperspectral Images making use of a High Resolution Color Image", IEEE Journal of Selected Topics in Applied Earth Observations and Remote Sensing, vol. 6, No. 2, Apr. 2015. (Year: 2015).*
Wu et al., "An Improved Subpixel Mapping Algorithm Based on a Combination of the Spatial Attraction and Pixel Swapping Models for Multispectral Remote Sensing imagery", IEEE Geoscience and Remote Sensing Letters, vol. 15, No. 7, Jul. 2018. (Year: 2018).*
Su et al., "Combining Pixel Swapping and Simulated Annealing for Land Cover Mapping", Sensors 2020, (20), Mar. 2020. (Year: 2020).*
Su et al., "A Sub-pixel Mapping Method Based on Logistic Regression and Pixel-Swapping Model", IGARSS 2019—2019 IEEE International Geoscience and Remote Sensing Symposium, 2019. (Year: 2019).*
Zheng et al., "Super-resolution of Mammograms", 2010 IEEE Symposium on Computational Intelligence in Bioinformatics and Computational Biology, 2010. (Year: 2010).*
Atkinson, Peter M. "Resolution manipulation and sub-pixel mapping." Remote sensing image analysis: Including the spatial domain. Springer, Dordrecht, 2004. 51-70 (Year: 2004).*
Todd, et al.; Model Predictive Filtering for Improved Temporal Resolution in MRI Temperature Imaging; Magn Reson Med.; May 2010; 63(5): 1269-1279; doi: 10.1002/mrm.22321; 27 pages.
International Search Report and Written Opinion regarding International Patent Application No. PCT/US2021/056444, dated Jan. 26, 2022.
Mertens KC et al: "Direct sub-pixel mapping exploiting spatial dependence", Geoscience and Remote Sensing Symposium, Anchorage, AK, USA Sep. 20-24, 2004, IEEE, vol. 5, Sep. 20, 2004 (Sep. 20, 2004), pp. 3046-3049.
Jian Zhang et al: "Exploring some issues of sub-pixel mapping based on directly spatial attraction", Geoscience and Remote Sensing Symposium, IEEE, Piscataway, NJ, USA, Jul. 25, 2010 (Jul. 25, 2010), pp. 339-342.
Smith M. R. et al: "Efficient algorithms for generating interpolated (zoomed) MR images", Magnetic Resonance in Medicine, vol. 7, No. 2, Jun. 1, 1988 (Jun. 1, 1988), pp. 156-171.
Atkinson PM: "Chapter 12: Mapping sub-pixel boundaries from remotely sensed images", Innovations in GIS 4: Selected Papers From the Fourth National Conference on GIS Research UK; Canterbury; UK, vol. 4, Jan. 1, 1997 (Jan. 1, 1997), pp. 166-180.
Mertens Koen et al: "A sub-pixel mapping algorithm based on sub-pixel/pixel spatial attraction models", International Journal of Remote Sensing, Basingstoke, Rants, GB, vol. 27, No. 15, Jan. 1, 2006 (Jan. 1, 2006), pp. 3293-3310.

* cited by examiner

FIG. 6

SYSTEM AND METHOD FOR ACQUIRING AND DISPLAYING AN IMAGE OF A SUBJECT

FIELD

The present disclosure relates to analyzing and displaying an image a subject, and particularly to a system to display an image based on image data acquired of the subject.

BACKGROUND

This section provides background information related to the present disclosure which is not necessarily prior art.

A subject, such as a human patient, may select or be required to undergo a procedure to correct or augment an anatomy of the subject. A surgeon can perform the procedure on the subject with images, such as viewing, of the subject. The images may be acquired using imaging systems such as a magnetic resonance imaging (MRI) system, computed tomography (CT) system, fluoroscopy (e.g. C-Arm imaging systems), or other appropriate imaging systems.

Images of a subject can assist a surgeon in performing a procedure including planning the procedure and performing the procedure. A surgeon may select a two dimensional image or a three dimensional image representation of the subject. The images can assist the surgeon in performing a procedure such as providing selected information to the surgeon. The images are generally provided by the imaging system at a selected resolution.

SUMMARY

This section provides a general summary of the disclosure, and is not a comprehensive disclosure of its full scope or all of its features.

Disclosed herein is a system for illustrating data for viewing by a user. The data may include an illustration of various features such as edges, temperature boundaries, or the like. In various embodiments, data may be collected with a selected system and illustrated at a raw or collection system resolution. Disclosed is a system to increase the displayed resolution of the data for viewing by the user.

In various embodiments, image data may be acquired of the subject. The image data may include and/or be directed to temperature data. Temperature data may be collected with a selected system that includes the same or different system. The temperature data may be collected at a selected resolution, such as the resolution of an imaging system. In various embodiments, a magnetic resonance system may be used to acquire data of a subject. The magnetic resonance data may include magnetic resonance thermometry (MRT) that may be acquired with and/or separate from magnetic resonance image (MRI) data. Regardless, the MRT data may be displayed at a selected resolution, such as based or determined by a resolution of the system. The resolution of the MR system may be based upon an acquisition speed and/or slice resolution. Accordingly, a higher resolution may require a greater time for data acquisition.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
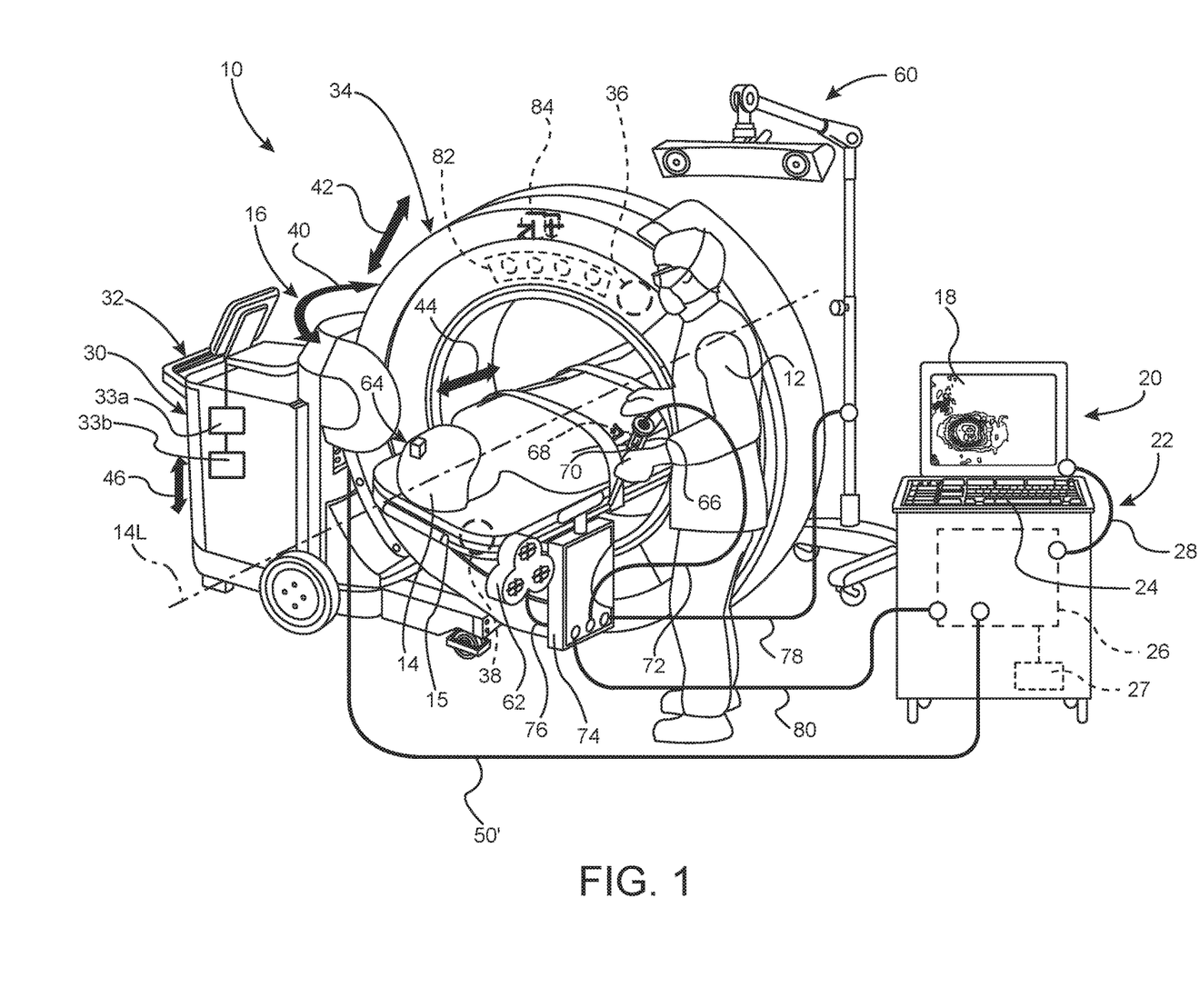
FIG. 1 is an environmental view of an imaging system in an operating theatre.

With reference to FIG. 1, in an operating theatre or operating room 10, a user, such as a surgeon 12, may perform a procedure on a subject 14, such as a patient. In performing the procedure, the user 12 can use an imaging system 16 to acquire image data of the patient 14 to allow a selected system to generate or create images to assist in performing a procedure. The image data may be generated by a selected imaging system, as discussed herein, for generating one or more projections of the subject 14. It is understood, however, that various types of image data may be collected and that the various types of image data may be used to generate or reconstruct an image 18. Image data types may also include other types of image data including magnetic resonance image data, temperature related image data, etc. The various types of image data may be used to generate one or more images for viewing by the user 12 or other appropriate person or for saving for later review, as discussed herein. In various embodiments, the image data is rendered to create or generate the images 18 for display with a display device.

The image 18 may include a model (such as a three-dimensional (3D) image) that can be generated using the image data and displayed as the image 18 on a display device 20. The display device 20 can be part of and/or connected to a processor system 22 that includes an input device 24, such as a keyboard, and a processor 26 which can include one or more processors or microprocessors incorporated with the processing system 22. The processing system 22 may further include selected types of non-transitory and/or transitory memory 27. A connection 28 can be provided between the processor 26 and the display device 20 for data communication to allow driving the display device 20 to display or illustrate the image 18. The processor may include a general purpose processor or a specific application processor and a memory system (e.g. a non-transitory memory such as a spinning disk or solid state non-volatile memory). For example, the memory system may include instructions to be executed by the processor to perform functions and determine results, as discussed herein.

The imaging system 16 may have various portions, such as those of an O-Arm® imaging system sold by Medtronic Navigation, Inc. having a place of business in Louisville, Colo., USA. The imaging system 16 may also include and/or alternatively include various portions such as those disclosed in U.S. Patent App. Pubs. 2012/0250822, 2012/0099772, and 2010/0290690, all incorporated herein by reference. The imaging system may also include a magnetic imaging system (MRI), computer tomography, ultrasound, or other appropriate imaging systems The imaging system 16 may include a mobile cart 30 to allow the imaging system to be mobile. The imaging system 16, however, may also be substantially stationary, in various embodiments. The imaging system 16 may further include a controller and/or control system 32. The control system 32, in various embodiments, may be incorporated into the cart 30 or other appropriate location. Further, the control system 32 may include a processor 33a and a memory 33b (e.g. a non-transitory memory). The memory 33b may include various instructions that are executed by the processor 33a to control the imaging system, including various portions of the imaging system 16.

In various embodiments, if the imaging system 16 is a MRI, it may include generally known MRI components. These may include one or more magnets, selected gradient coils, and radiofrequency coils. The controller 32 may be used to operate and control the MRI for the acquisition of image data. The controller 32 may also be used to generate images in addition or alternatively to the processor 22. The imaging system 16 may include a gantry to hold or house one or more of the components.

In various embodiments, the imaging system 16 may include the imaging gantry 34 to have positioned therein a source unit or system 36 and a detector 38 may be connected to the mobile cart 30. In various embodiments, the source 36 may be a duel energy source for a dual energy imaging systems such as those disclosed in U.S. Pat. App. Pub. Nos. 2012/0099768 and 2012/0097178, both incorporated herein by reference.

The gantry 34 may be O-shaped or toroid shaped, wherein the gantry 34 is substantially annular and includes walls that form a volume in which the source unit 36 and detector 38 may move. The mobile cart 30 can be moved from one operating theater to another and the gantry 34 can move relative to the cart 30, as discussed further herein. This allows the imaging system 16 to be mobile and moveable relative to the subject 14 thus allowing it to be used in multiple locations and with multiple procedures without requiring a capital expenditure or space dedicated to a fixed imaging system.

In various embodiments, the source unit 36 may be an x-ray source, also referred to as an emitter that can emit x-rays toward and/or through the patient 14 to be detected by the detector 38. As is understood by one skilled in the art, the x-rays emitted by the source 36 can be emitted in a cone and detected by the detector 38. The source/detector unit 36/38 is generally diametrically opposed within the gantry 34. The detector 38 can move in a 360° motion around the patient 14 within the gantry 34 with the source 36 remaining generally 180° opposed (such as with a fixed inner gantry or moving system) to the detector 38.

In various embodiments, the gantry 34 can move isometrically relative to the subject 14, which can be placed on a patient support or table 15, generally in the direction of arrow 40 as illustrated in FIG. 1. The gantry 34 can also tilt relative to the patient 14 illustrated by arrows 42, move longitudinally along the line 44 relative to a longitudinal axis 14L of the patient 14 and the cart 30, can move up and down generally along the line 46 relative to the cart 30 and transversely to the patient 14, to allow for positioning of the source/detector 36/38 relative to the patient 14. The imaging device 16 can be precisely controlled to move the source/detector 36/38 relative to the patient 14 to generate precise image data of the patient 14. The imaging device 16 can be connected with the processor 26 via connection 50 which can include a wired or wireless connection or physical media transfer from the imaging system 16 to the processor 26. Thus, image data collected with the imaging system 16 can be transferred to the processing system 22 for navigation, display, reconstruction, etc. In addition to or alternatively to the gantry 34 and or other portions of the imaging system 16 moving, the table 15 may move relative to the gantry 34.

According to various embodiments, the imaging system 16 can be used with an un-navigated and/or navigated procedure. In a navigated procedure, a localizer and/or digitizer, including either or both of an optical localizer 60 and an electromagnetic localizer 62 can be used to generate a field and/or receive and/or send a signal within a navigation domain relative to the patient 14. The navigated or navigational space or domain relative to the patient 14 can be registered to the image 18. Correlation, as understood in the art, is to allow registration of a navigation space defined within the navigational domain and an image space defined by the image 18. A patient tracker or dynamic reference frame 64 can be connected to the patient 14 to allow for a dynamic registration and maintenance of registration of the patient 14 to the image 18.

The patient tracking device or dynamic registration device 64 and an instrument 66 can then be tracked relative to the patient 14 to allow for a navigated procedure. The instrument 66 can include a tracking device, such as an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation/probe interface device 74 such as the electromagnetic localizer 62 with communication line 76 and/or the optical localizer 60 with communication line 78. Using the communication lines 74, 78 respectively, the interface 74 can then communicate with the processor 26 with a communication line 80. It will be understood that any of the communication lines 28, 50, 72, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of a tracked location of the instrument 66 relative to the image 18 for performing a procedure.

One skilled in the art will understand that the instrument 66 may be any appropriate instrument, such as a ventricular or vascular stent, spinal implant, neurological stent or stimulator, ablation device, or the like. In various embodiments, the instrument 66 may cause a temperature change in the subject 14. The instrument 66 can be an interventional instrument or can include or be an implantable device. Tracking the instrument 66 allows for viewing a location (including x,y,z position and orientation) of the instrument 66 relative to the patient 14 with use of the registered image 18 without direct viewing of the instrument 66 within the patient 14.

Further, the gantry 34 can include an optical tracking device 82 and/or an electromagnetic tracking device 84 to be tracked with the respective optical localizer 60 or electromagnetic localizer 62. Accordingly, the imaging device 16 can be tracked relative to the patient 14 as can the instrument 66 to allow for initial registration, automatic registration, or continued registration of the patient 14 relative to the image 18. Briefly, registration includes determining one or more points relative to the subject 14 (e.g. subject space) and points in the image 18 (e.g. image space). A registration map is then made between the two spaces to allow for a registration of the two spaces. The registration may be automatic, such as tracking the subject and the imaging system 16 during the collection of the image data. Regardless, the registration allows the tracking and illustration of a position of a tracked instrument in the subject space to be displayed (e.g. as an icon superimposed on the image 18) in the image 18 with the display device 20. Registration and navigated procedures are disclosed in U.S. Pat. No. 8,238,631, incorporated herein by reference. Upon registration and tracking of the instrument 66, an icon 90 may be displayed relative to, including superimposed on, the image 18.

Figure 2:
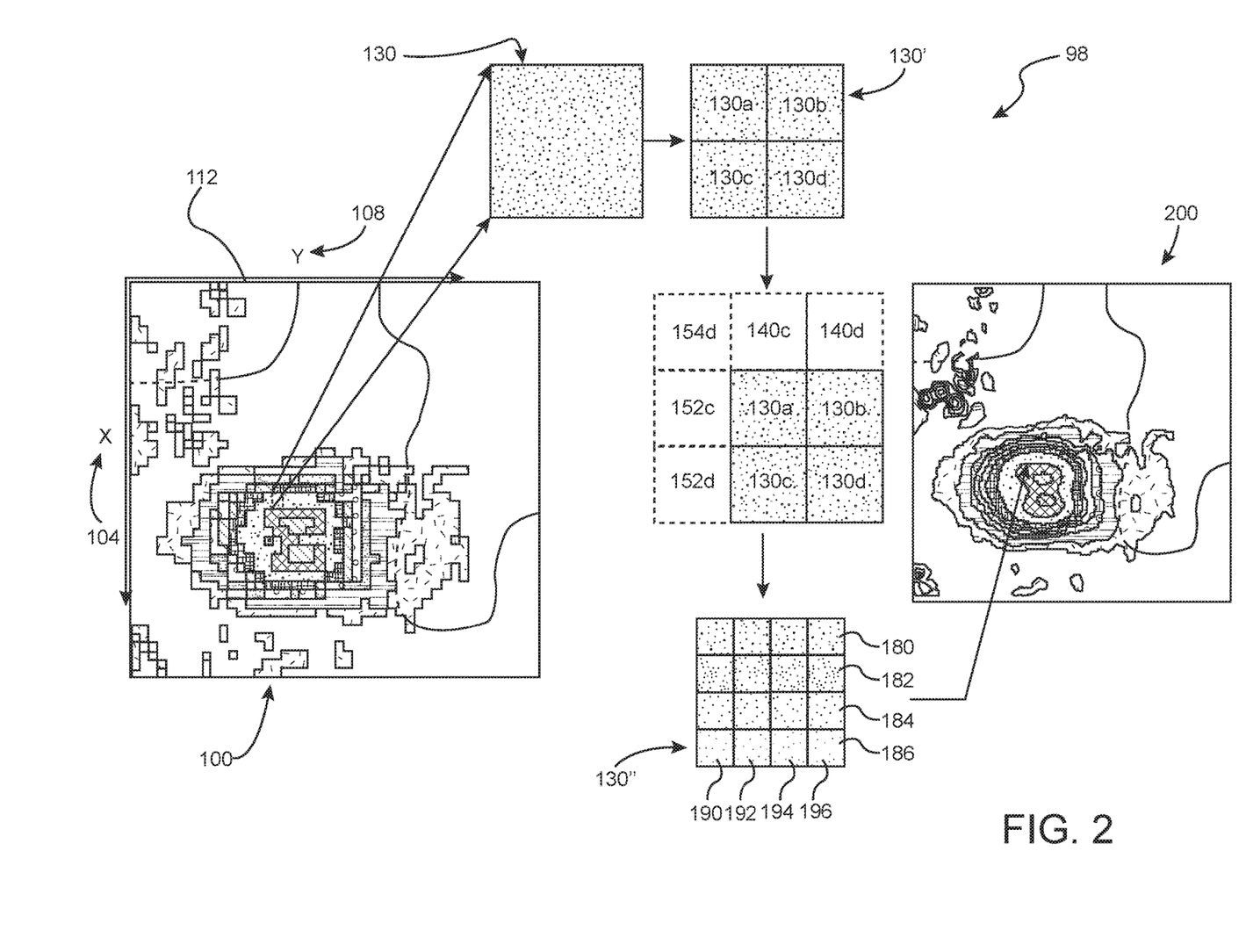
FIG. 2 is a graphical flow of a hyper-spatial determination process, according to various embodiments.

With continuing reference to FIG. 1, and additional reference to FIG. 2, the imaging system 16 may acquire image data of the subject 14, as discussed above. The imaging system 16 may also include various portions operated to collected selected data in addition to or alternatively to image data. In various embodiments, the image data acquired of the subject may include various or selected image data and/or other data of the subject 14, as discussed further herein, and/or acquired separately from the image data. In various embodiments, for example, thermometry data may be collected of the subject 14.

Thermometry data may include data regarding a temperature of various portions of the subject 14 that may be collected with MR systems. The MR system may collect data regarding a temperature or change in temperature of selected areas or regions of the subject 14. In various embodiments, for example, the imaging system 16 may include or be an MR system that may collect data regarding the subject 14. The MR system may collect data regarding a discrete temperature of the subject 14 and/or a change in temperature of the subject 14. Accordingly, data may be collected of the subject 14 regarding a temperature of a selected portion of the subject 14.

With reference to FIG. 2, a visual flow chart or diagram illustrates a selected set of information that may be collected regarding the subject 14 with the imaging system 16, particularly if the imaging system 16 is or includes a thermometry system. The imaging system 16 may collect an initial or raw data scan 100 of the subject 14. The raw data may include thermometry information that is collected at a selected resolution. The selected resolution may include an overall size or pixel size of the raw scan, such as about 400 pixels by 400 pixels. The dimensions may be two dimensional, including a X direction 104 and a Y direction 108. In various embodiments, for example, the raw image 100 may include a pixel density of about 400 pixels by about 400 pixels in the two directions X,Y. Accordingly, the raw thermometry image 100 may include a pixel size in the X direction 104 of about 400 pixels and a density of about 400 pixels in the Y direction. Thus, the raw thermometry image 100 may include pixel information of about 160,000 pixels. Each pixel in the raw thermometry image data 100 may include a temperature information, including a discrete temperature and/or a change in temperature. In other words, each pixel in the data 100 may include a temperature value. It is understood, however, that other data may be collected and the pixel may include a value for any selected data.

The raw image 100 may be collected based upon use of the imaging system 16. The imaging system 16 may collect the thermometry data in the X and Y direction, as illustrated in FIG. 2. The imaging system 16 may include or collect data regarding the pixels for the raw image data 100. The pixel thermometry data may then be superimposed and/or placed on an image, such as an image 112. The image 112 may include an image of the subject 14, such as a MRI brain scan, bone scan, etc. The raw thermometry 100 and/or the image 112 may be displayed as the image 18 on the display device 20 and/or a refined (e.g. hyper-spatialized) or selected thermometry image, as discussed further herein. Nevertheless, the thermometry image 100 and a selected image 112 of the subject 14 may be displayed on the display device 20 for viewing by the user 12.

The raw thermometry data 100 may include the selected pixels, as discussed above. The raw thermometry data 100, therefore, includes a plurality, such as about 160,000 pixels. A pixel 130 is an exemplary pixel from the raw thermometry data 100, and is understood not to represent all thermometry image pixels therein. Rather, the pixel 130 is merely exemplary of possible thermometry data that may be analyzed and/or displayed, as discussed further herein. The thermometry pixel 130, however, may include various data regarding a temperature of the temperature within the raw thermometry data 100.

Generally, the raw thermometry data 100 includes the selected pixels, such as the pixel 130, all of which are determined to have a temperature. In various embodiment, a selected temperature range is not displayed and therefore appear "invisible". As discussed further herein, the temperature may include a selected discrete temperature and/or a temperature change (e.g. a delta temperature) relative to a previously determined or acquired temperature. Therefore, each of the pixels 130 include a selected single temperature. The pixel 130 may be displayed on the display device 20 in a selected manner to represent the selected temperature. The display device 20 may display the pixel 130 with a selected color, blink rate, grey scale, crosshatch, fill design, and/or other appropriate distinction to distinguish the pixel 130 from adjacent pixels having the same and/or different temperatures.

Figure 3:
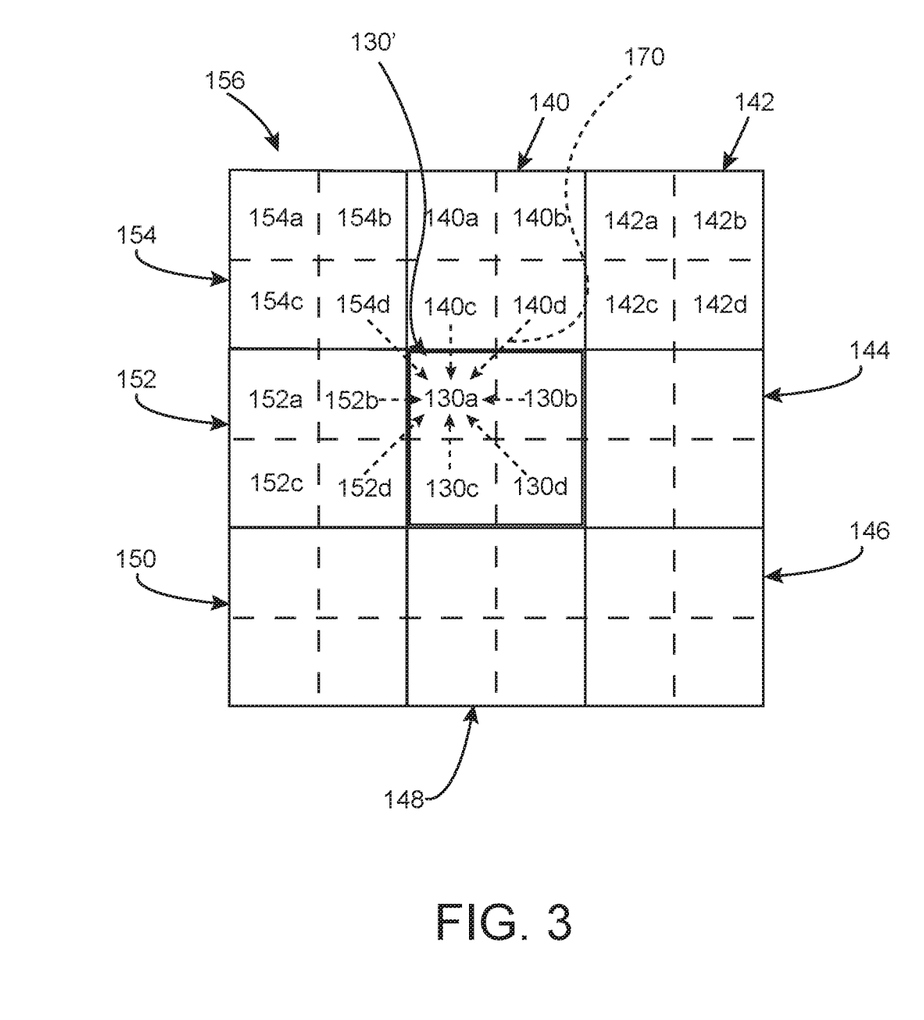
FIG. 3 is a detailed view of a first division of a pixel and bounding pixels, according to various embodiments.

With continuing reference to FIG. 2, and additional reference to FIG. 3, the pixel 130 may represent a single temperature in the raw pixel or thermometry data 100. According to the process as illustrated in FIG. 2, however, the pixel 130 may be divided to be reformatted to a reformatted or hyper-spatial pixel 134. The hyper-spatial pixel 134 may include various segments, such as subpixel segments, as discussed further herein. The hyper-spatial pixel 134 may be determined using the flow schematic 98.

The single pixel 130, as discussed further herein, may be an exemplary pixel of the raw pixel thermometry data 100. It is understood that each of the pixels in the raw data 100 may be analyzed and/or hyper-spatialized as discussed further herein. Accordingly the discussion of the single pixel 130 is merely exemplary. The process may be applied to all pixels in the raw thermometry data 100.

The single pixel 130, therefore, may be initially divided into a selected number of portions that may also be referred to as pixel elements or subpixels. In various embodiments, the division may be into quadrants, including four subpixels 130*a*, 130*b*, 130*c*, and 130*d*. The subpixels 130*a*-130*d* may then be analyzed. Analysis of the pixel portions 130*a*-130*d* may include information of pixels outside of the pixel 130.

In various embodiments, the single pixel 130 is bounded by a number of pixels, such as other pixels, particularly around an edge and/or corner of the pixel 130. As illustrated in FIG. 3, bounding pixels 156 may include pixels 140, 142, 144, 146, 148, 150, 152, and 154. Accordingly, for a square pixel the single pixel 130 may have edge boundary pixels 140, 144, 148 and 152 and corner boundary or touching pixels 142, 146, 150, and 154. Thus, the single pixel 130 may be bounded by eight pixels 140-154. Each of the bounding pixels 140-154 (referred to herein as bounding pixels 156) may include or be referred to analyze the single pixel 130. For example, the bounding pixels 140, 152 and 154 all touch or contact the pixel quadrant 130a. Similarly the pixels 140, 142, 144 touch or bound the pixel segment 130b. The pixel segment 130d is bounded by the pixels 144, 146, 148. And finally the pixel segment 130c is bounded by the pixels 148, 150, 152.

The pixel 130, therefore, may be analyzed and evaluated to determine a temperature of the specific pixel portion 130a. Each pixel portion may be assigned the temperature of the whole pixel. In various embodiments, the temperature of the pixel portion 130a may be determined to be an average of the pixel 130 and that of the bounding pixels 140, 152, and 154. The pixel segment 130a, therefore, may then include or be reevaluated to include the average temperature of the pixels 130, 140, 152, and 154. Similarly each of the pixel segments 130b, 130c, and 130d may be resampled to include or be assigned the average temperature of the bounding pixels and/or pixel portions relative thereto. Accordingly, each of the pixel portions 130a-130d may be reassigned a temperature based upon an average of the pixel temperature 130 and the respective bounding pixels, as discussed above. Therefore, while the pixel 130 may have a single temperature assigned thereto, each of the subpixel elements 130a-130d may be assigned a different temperature based upon the determined or evaluated temperatures due to the averaging of the bounding pixels.

Also, as discussed herein, each pixel portion 130a-130d may be assigned a value that is an average of it and the pixel portions that bond it. The average temperature may be determined by evaluating the value of the pixel portions of the pixel 130 and the respective bounding pixel portions. As discussed herein, each bounding pixel may also be dividing into respective pixel portions. As illustrated in FIG. 3, the pixel portion 130a may be reassigned a value (e.g. temperature value) of the bounding pixel portions 130b, 130c, 130d, 152d, 152b, 154d, 140c, 140d, and 130a. The value of the pixel portions may be summed, as illustrated by the arrows 170, and then divided by the number of pixel portions to determine an average value of the pixel portion 130a.

Figure 4:
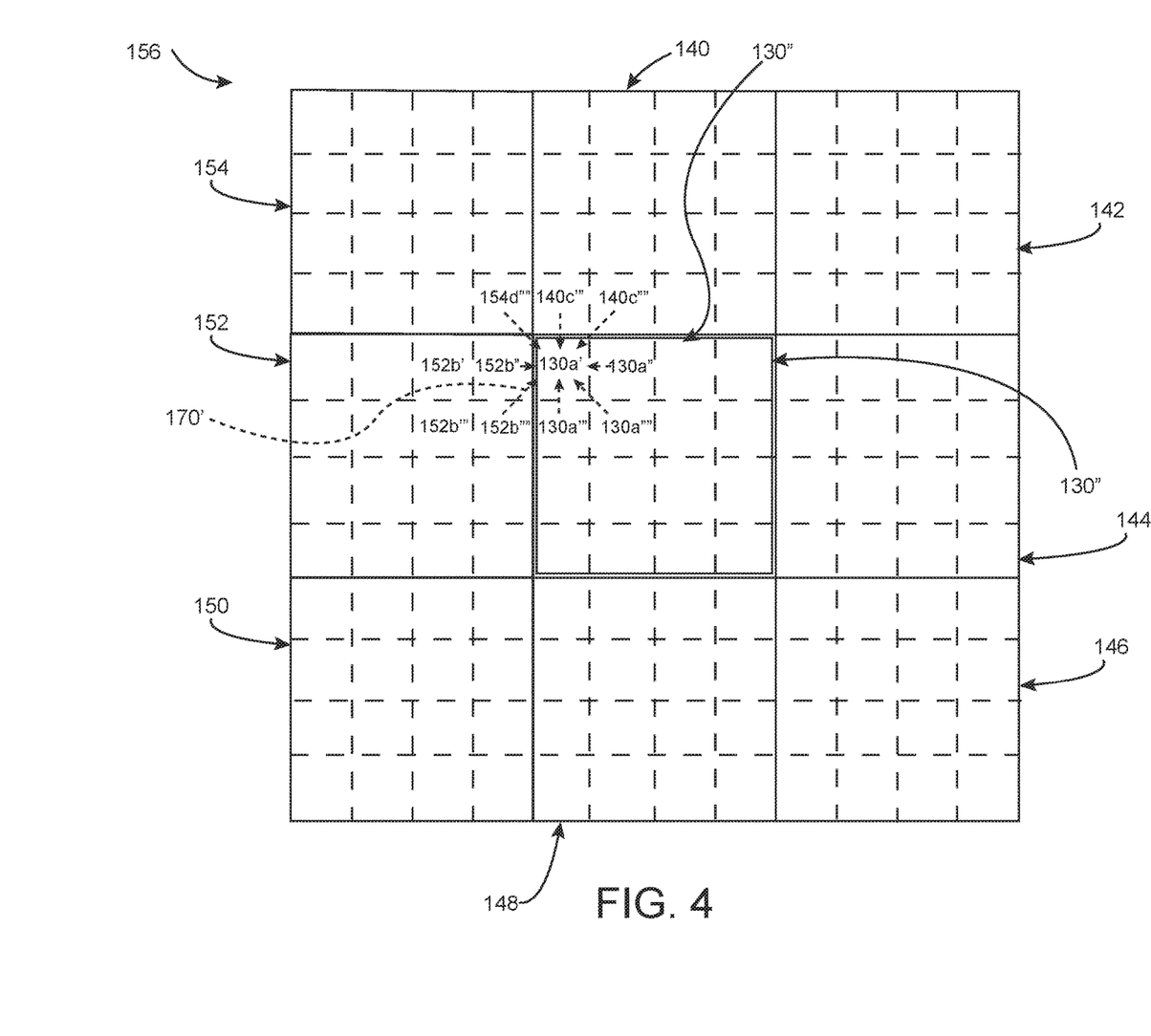
FIG. 4 is a detailed view of a second division of a pixel and bounding pixels, according to various embodiments.

With continuing reference to FIGS. 1-3, and additional reference to FIG. 4, the initial pixel 130 may be further subdivided into selected pixel elements, as illustrated in FIG. 4. For example, each of the first pixel portions 130a-130d may be further divided, such as into second pixel portions which may be quadrants of the first pixel portions. This may be referred to as a hyper-spatial pixel 130".

The subdivided or hyper-spatial pixel 130" may be the initial pixel 130 that is subdivided into at least a selected number of subpixel portions or elements, such as sixteen subpixel elements. Each of the subpixel elements may be referred to as quadrants of the initial subpixel elements 130a-130d augmented by one or more """. For the following discussion, therefore, the subpixel element 130a may be subdivided into four hyper-spatial elements 134a augmented by ', thus four hyper-spatial elements 130a', 130a", 130a''', and 130a"" may be defined. Therefore, the hyper-spatial pixel 134 may include four rows and four columns of pixel portions, as illustrated in FIG. 2 and FIG. 4. The initial pixel 130 that may be formed into the initial or first subdivided pixel 130' and then may be subdivided into the hyper-spatial pixel 130" may allow for determining of a temperature of $\frac{1}{16}^{th}$ of the original pixel 130. As illustrated in FIG. 2 and FIG. 4, the hyper-spatial 130" may be divided into at least sixteen pixel segments or portions. Accordingly, the raw pixel image 100 may be subdivided into about 2,560,000 pixel elements or portions by subdividing each pixel into at least sixteen pixel elements or portions, as illustrated at FIG. 2 and FIG. 4.

The hyper spatial or second pixel portions may also be assigned a selected value, such as an average temperature. As discussed above, the initial pixel 130 may have the four quadrants or portions 130a-130d assigned a selected temperature based upon an averaging of the pixels or pixel portions contacting or adjacent to each of the pixel segments 130a-130d. Each of the pixel elements 130a-130d may be divided into at least four segments, for example, identified by 130a', 130a", 130a''', and 130a ". Each of the hyper-spatial elements 130a'-130a"" may then have a value assigned to each, such as an averaged temperature based upon the selected and adjacent hyper-spatial pixels relative thereto. Accordingly, each of the adjacent or bounding pixels may also be subdivided into hyper-spatial elements and each of these respective elements may be used to average or determine an average temperature of hyper-spatial elements of the pixel 130". For example, the hyper-spatial element 130a' may be averaged based upon the hyper-spatial elements adjacent thereto including the hyper-spatial elements 130a", 130a''', 130a"", 152b"", 152b''', 154d"", 154c"", and 154c''''. As illustrated in FIG. 4, the hyper-spatial element 130a' may have an average temperature determined from adjacent hyper-spatial portions identified with an averaging arrow 170' from each of the respective adjacent hyper-spatial elements. The average may include the pixel portion to which the value is to be applied and those that are adjacent to it. Adjacent pixels or pixel portions, regardless of the size, touch at least one portion of the selected pixel, such as an edge or corner.

It is understood that each of the hyper-spatial elements of the pixel 130", and the other pixels in the initial image 100 may be averaged based upon or in the same manner. Accordingly, each pixel may have a selected number of elements, such as sixteen pixel elements, each having a temperature assigned thereto for defining each pixel at sixteen pixel elements with a separate discrete temperature therefor. Thus, the above discussion is not limited to the pixel 130, but may be applied to each pixel in the raw data 100.

Hyper-spatial elements of 130a'-130a"" may each be reassigned or assigned a selected temperature based upon an average from the adjacent hyper-spatial elements of other pixels. Accordingly, as illustrated in FIG. 4, the hyper-spatial element may form the hyper-spatial pixel 130". With continuing reference to FIG. 4 and returning reference to FIG. 2, the hyper-spatial pixel 130" includes sixteen pixel elements aligned in four rows 180, 182, 184 and 186, respectively. The pixels are also aligned in four columns 190, 192, 194, 196. Accordingly, the hyper-spatial pixel 130' includes the sixteen pixel elements that have been assigned a temperature based upon the averaging, as discussed above in relation to FIG. 4. The hyper-spatial pixel 130, however, including the sixteen hyper-spatial elements includes the same dimensions as the pixel 130 from the raw thermometry data 100. Accordingly, the overall dimensions of the hyper-spatial pixel 130 including all of the four rows 180-186 and all of the four columns 190-196, includes the same dimensions in the X dimension 104 and Y dimension 108 as the original pixel or initial pixel 130. Thus, the hyper-spatial pixel 130" may be included in a rendering or re-rendering of the thermometry data in combination with other pixels of the same size that may include original or initial size pixels and/or other hyper-spatial pixels.

Figure 5:
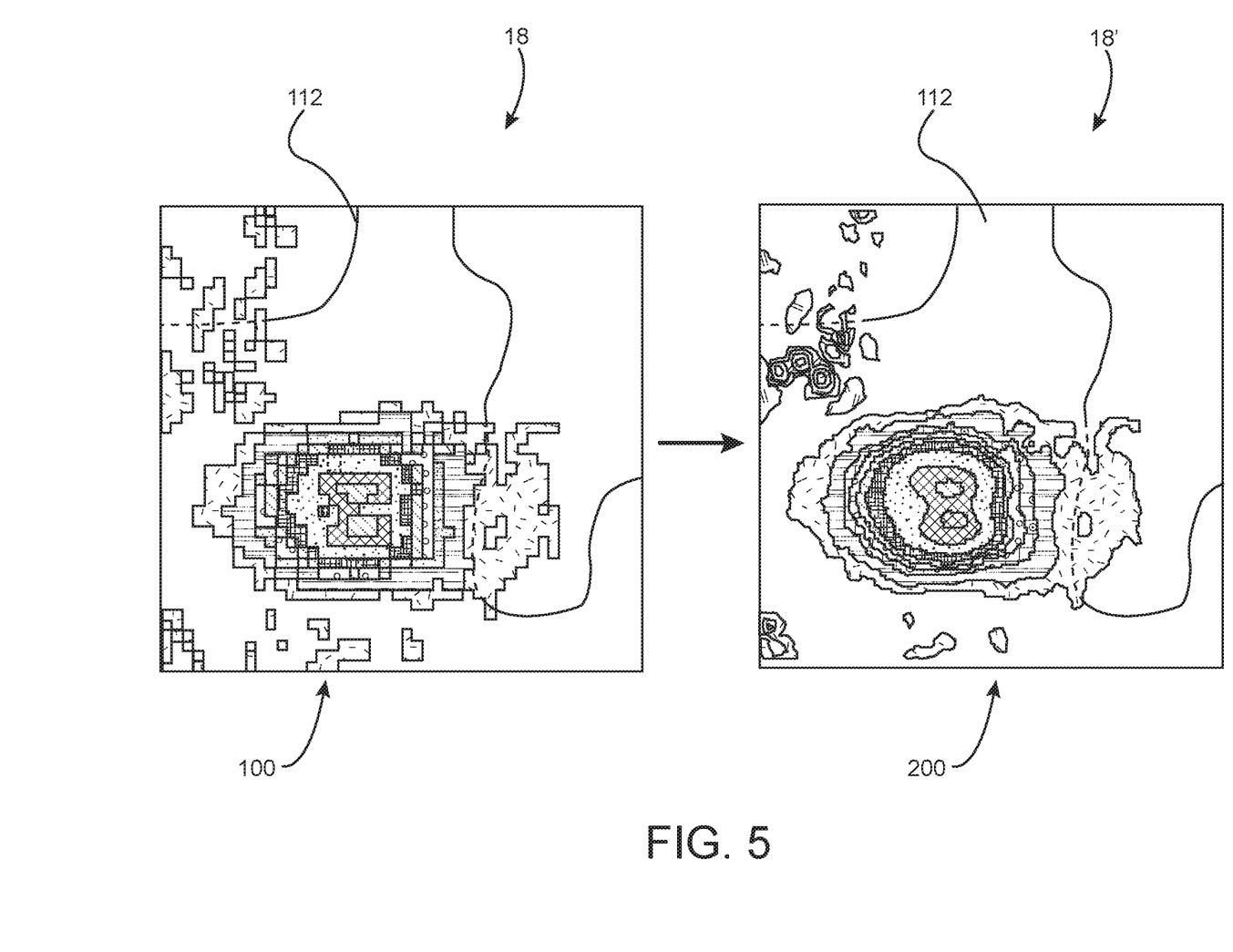
FIG. 5 is an initial and hyper-spatial display of selected data, according to various embodiments.

With continuing reference to FIG. 2 and additional reference to FIG. 5, the initial thermometry data may be re-rendered or reconstructed to a higher resolution or hyper-spatial image 200. As discussed above, the thermometry information, as either the initial thermometry information 100 or the hyper-spatial information 200 may be displayed on or relative to an image 112. As illustrated in FIG. 5, the initial thermometry data may display determined temperatures at the pixel level, including the pixel 130. The pixel 130 includes the dimensions X and Y, 104, 108 that may be based upon the slice size, scan speed, or the like. The re-rendered thermometry image 200 may include the pixel 130 re-rendered as the hyper-spatial pixel 130", thus including a resolution of sixteen times that of the original pixel 130. The hyper-spatial pixel 130, including the sixteen pixel elements, each include thermometry information that may be output, such as being displayed, as individual pixels on the or in the hyper-spatial image 200. The hyper-spatial thermometry information 200 may also be overlaid on the image 112, such as with the display device 20, for viewing by the user 12. Thus, the thermometry information may be viewed as having a greater resolution and with more refinement for consideration by the user 12. The image 112 may have superimposed or positioned or displayed relative thereto the hyper-spatial thermometry information 200.

The thermometry information may relate to various procedures, such as an ablation procedure, a therapy delivery procedure, or other appropriate procedures. For example, the instrument 66 may include an ablation instrument that is positioned in a selected portion of the subject, such as within a cranium or brain tissue of the subject 14. An increase in temperature may be achieved through a selected appropriate manner. The thermometry data may be determined and displayed for viewing by the user 12. The thermometry data may be collected as the selected resolution, such as including the pixel size 130. The selected processor systems, such as the processor system 26, may evaluate the thermometry data to generate the hyper-spatial pixel 130". As is understood by one skilled in the art, the process may be applied to all of the pixels or a selected region of interest of pixels in the hyper-spatial image thermometry data 100. Accordingly, a selected number or all of the pixels may be evaluated to generate the hyper-spatial pixel for each of the pixels in the initial data. Thus, each of the pixels having being reformatted into the hyper-spatial form may be re-rendered and displayed on the image as the hyper-spatial thermometry data 200.

Figure 6:
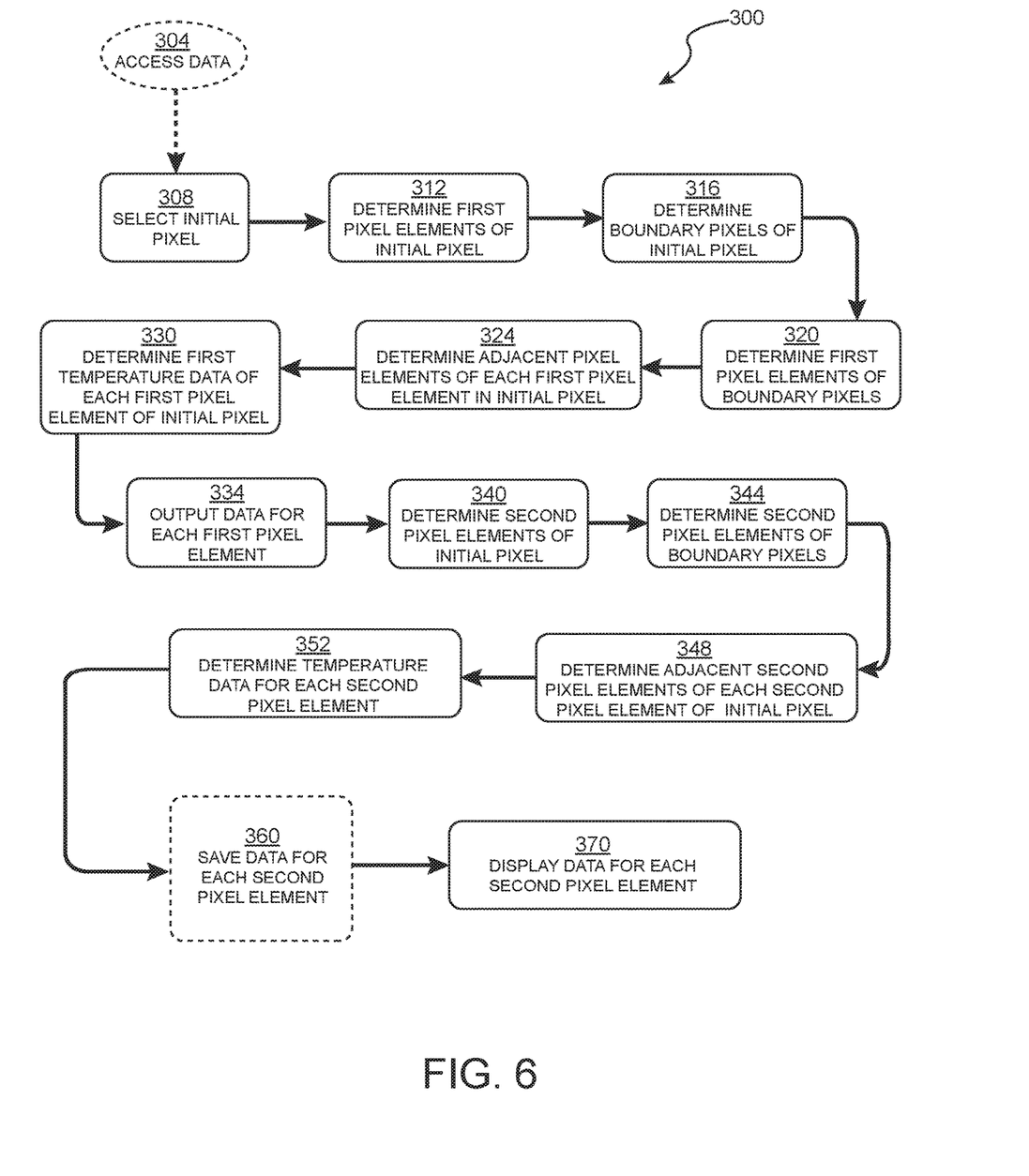
FIG. 6 is a flow chart of the method for generating hyper-spatial data.

Turning reference to FIG. 6 and with continuing reference to FIGS. 2-5, a flow chart 300 illustrates and summarizes the method, as discussed above, to generate the hyper-spatial or pixel elements 130" from the initial pixel 130. Accordingly, the method 300 may first include accessing selected data, such as the initial data 100, in block 304. It is understood that the process 300 does not require accessing of the data and may simply include the process as discussed further herein, however, access to the data in block 304 may be used to collect or make for the determinations. Accessing data may include acquiring data with a system, such as an MR system, and/or recalling data from a prior acquired acquisition. Nevertheless, selecting an initial pixel in block 308 allows for a determination (e.g. selection) of a pixel. The pixel may be manually selected and/or automatically selected. In various embodiments, as discussed above, the process may be applied to all pixels in the raw data 100. Thus, all pixels may be selected in a selected manner and/or at once for a simultaneous analysis.

As discussed above, the pixel 130 may be an exemplary pixel that is selected as the initial pixel. In various embodiments, as also discussed above, each pixel in the initial data 100 may be analyzed and evaluated according to the method 300. Accordingly, the selection of the initial pixel in block 308 may be a search pattern or grid pattern selection of all pixels in the initial data 100 and the initial pixel, such as the pixel 130, may be any or all pixels to which the method 300 may be applied substantially independently and/or simultaneously. Nevertheless, the selection of a pixel, such as the pixel 130, for the discussion of the method 300 may be exemplary made in block 308.

A determination of a first pixel element (also referred to as pixel portion) of the initial pixel is made in block 312. The initial pixel elements may include the initial pixel elements where the initial pixel is divided into quadrants, such as in the first initial pixel element 130'. Thus, the initial pixel elements may include the initial pixel elements 130a-130d. Also and/or simultaneous with determining the initial pixel bounding pixel may also be selected or determined in block 316. Bounding the pixels may be pixels that are adjacent to and/or contact at least a portion of the initial pixel 130. The bounding pixels 156, as illustrated in FIG. 3, may be the determined or selected bounding pixels in block 316.

Determination of first pixel elements of the bounding pixels may then be made in block 320. Again, the bounding pixels 156 may each include bounding pixel elements, as discussed above and illustrated in FIG. 3. The bounding pixel elements may also all be identified relative to first pixel elements that they are adjacent to or contact, such as on an edge or a corner, as also illustrated in FIG. 3.

After determining the first pixel elements of the initial pixel and the bounding pixels in blocks 316, 320 a determination of adjacent pixels to each pixel element may be made in block 324. The adjacent pixel elements may include those that contact an edge of a selected pixel element and/or a corner of a pixel element. Accordingly, as illustrated in FIG. 3, the first pixel element 130a may have selected adjacent pixels or determined adjacent pixel elements. The adjacent pixel elements of pixel element 130a may include pixel elements 130b, 130c, 130d, 152d, 152b, 154d, 140c, and 140d. The determination of the adjacent pixels may include edge detection and/or corner detection and/or contact detection.

After determining the adjacent pixels in block 324 a determination of a temperature data for each pixel element of the initial pixel is made in block 330. The determination of the temperature data for each pixel element includes the process, as discussed above. The adjacent pixels, as discussed above, may each be averaged with the pixel element to which they are adjacent. As discussed above, each of the adjacent pixels may be averaged (e.g. summed and divided by the number of adjacent pixels) as schematically illustrated by the averaging arrows 170. Accordingly, the determination of a temperature data for each pixel element may include the averaging of adjacent pixel elements for the respective pixel element at the initial pixel.

Optionally, the value, e.g. the temperature, of the first pixel elements may be output in block 334. The output may include saving, such as in a memory system, the values. Other outputs, may include displaying the determined values.

Determination of second pixel elements (also referred to as second pixel portions) may then be made in block 340.

Determination of second pixel elements may include dividing the initial pixel elements or first pixel elements from block 312 into further quadrants, as discussed above. For example, with reference to FIG. 4, the initial pixel element 130a may be divided into second pixel elements 130a'-130a''''. The determination of the second pixel elements may be made for each of the initial pixel elements in the initial pixel. Further, determination of second pixel elements for the bounding pixel elements is made in block 344. Again, with reference to FIG. 4, each of the pixel elements in the bounding of pixels and respective first pixel elements may also be divided into second pixel elements. Therefore, the initial data 100 may be subdivided into a first set of pixel elements and a second set of pixel elements, as discussed above and according to the method 300.

A determination of adjacent second pixel elements to each second pixel element to the initial pixel is then made in block 348. The adjacent second pixel elements may be similar to the adjacent first pixel elements, again contacting sides or corners of a selected second pixel element. As illustrated in FIG. 4, the second pixel element 130a' includes the adjacent pixel elements 130a'', 130a''', 130a'''', 152b'''', 152b'', 154d'''', 140c''', and 140c''''. The adjacent second pixel element may be identified through various processes, such as edge detection and distance relative to the selected second pixel element of the initial pixel. Once the determination of adjacent second pixel elements is made in block 348 a determination of temperature of a selected or each second pixel element is made in block 352.

The determination of temperature data for each second pixel element may be performed in a manner similar to that discussed above. As discussed above, each of the first pixel elements may be assigned selected temperature data. Accordingly, each of the second pixel elements that have been divided from the first pixel element may include the same temperature data. The selected second pixel element may be reassigned a temperature data based upon an averaging of the adjacent second pixel elements. As illustrated in FIG. 4, the schematic averaging arrows 170' illustrated the averaging of the temperature data to the selected second pixel element 130a'. The averaging may include a summing of all of the second pixel elements that are adjacent to the selected second pixel element and dividing by the number of second pixel elements. Accordingly, the averaging may include a summing of all nine pixel elements and dividing the value by nine to determine a temperature data for the selected second pixel element 130a'.

Once the determination of temperature data for the second pixel elements is made in block 352, the second pixel element data or temperature data may be saved in block 360. The saving of the data in block 360 is optional, and need not be performed for the method 300. However, the temperature data may be saved for selected purposes, such as later analysis and/or transmission to an alternative location.

Additionally, and/or alternatively to saving the data in block 360, the temperature data may be displayed in block 370. As discussed above, the re-rendered or second rendering of the temperature data 200 may be displayed as the image 18' on the display device 20 for viewing by the user 12 or other appropriate individual. Accordingly, the user 12 may view the re-rendered temperature data 200 relative to selected image data 112, as discussed above.

The method 300, therefore, allows the user 12 to collect selected temperature data and have it rendered for display for viewing with the display device 20. It is understood that the user may operate the selected system, such as the processor 26, for collection and/or rendering of the temperature data for viewing by the user 12. It is further understood that the system may automatically render the collected image data for display and viewing by the user 12 according to the various processes. Thus, the processor system 26 may execute instructions to perform the method 300, as discussed above, substantially automatically, with input from a user, or with partial input from the user such as the user selecting a procedure for which the re-rendering of the data is performed. Regardless, the processor system 26 may execute instruction in line with the discussion above, including the flow chart 300, for re-rendering the temperature data as the hyper-spatial image 200.

It is further understood that further sub-pixels or divisions of pixel elements may be made, such as generating a third set of pixel elements including four pixel elements for each of the second pixel elements. The further division may create sixty-four third pixel elements from the original pixel 130, or any appropriate initial or original pixel. Thus, the method 300 may allow for a further refinement or a division of the temperature data for selected purposes.

As discussed above, a selected value (e.g. a temperature value) may be assigned to a selected pixel or pixel portion. It is understood by one skilled in the art that the value may be assigned to any appropriate portion, such as a face or portion of a three dimensional portion or element as well. Accordingly, the selected value may be averaged from elements or portions adjacent to a selected portion or element and the value assigned to the selected element.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a special purpose computer created by configuring a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor or module or 'controller' may be replaced with the term 'circuit.' The term 'module' may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of generating hyper-spatial temperature data of a patient, comprising:
   selecting a first pixel;
   determining bounding pixels of the first pixel;
   dividing the first pixel into a plurality of first pixel portions;
   dividing each of the bounding pixels into a plurality of respective bounding first pixel portions;
   selecting at least a sub-plurality of the first pixel portions of the plurality of first pixel portions and a sub-plurality of respective bounding first pixel portions of the plurality of respective bounding first pixel portions as adjacent pixel portions to a selected one first pixel portion of the plurality of first pixel portions;
   determining a value for the selected one first pixel portion based on the adjacent pixel portions; and
   outputting the determined value;
   wherein the determined value of the selected first pixel portion includes a temperature;
   wherein outputting the determined value includes displaying the selected one first pixel portion with a display device;
   wherein a selected temperature range is not displayed and appears invisible on the display device.

2. The method of claim 1, wherein determining the value includes:
   determining an averaged value for each pixel in which the adjacent pixel portion initially existed; and
   applying the averaged value to the selected one first pixel portion.

3. The method of claim 1, wherein determining the value for the selected one first pixel portion based on the adjacent pixel portions includes executing instructions with a processor to determine the value.

4. The method of claim 3, wherein the determined value is based on a value of each pixel in which the adjacent pixel portion initially existed.

5. The method of claim 1, wherein dividing the first pixel into the plurality of first pixel portions includes determining quadrants of the first pixel, wherein each pixel portion of the plurality of pixel portions is one quadrant of the first pixel.

6. The method of claim 1, further comprising:
   dividing each first pixel portion of the first pixel into a plurality of second pixel portions;
   dividing each bounding first pixel portion of the plurality of respective bounding first pixel portions into a plurality of second bounding pixel portions;
   selecting at least a sub-plurality of the second pixel portions of the plurality of second pixel portions and a sub-plurality of respective bounding second pixel portions of the plurality of respective bounding second pixel portions as subsequent adjacent pixel portions to a selected one second pixel portion of the plurality of second pixel portions;
   determining a subsequent value for the selected one second pixel portion based on the subsequent adjacent pixel portions; and
   outputting the determined subsequent value.

7. The method of claim 6, wherein each second pixel portion of the plurality of second pixel portions includes a location within the first pixel.

8. The method of claim 7, wherein outputting the determined subsequent value includes displaying on the display device the plurality of second pixel portions at each second pixel portions location within the first pixel.

9. The method of claim 8, wherein the determined value is displayed as a color.

10. A method of generating a hyper-spatial temperature data of a patient, comprising:
    acquiring thermometry data regarding each pixel in an array of pixels;
    dividing each pixel in the array of pixels into a first plurality of first pixel portions;
    determining a first average value including:
       (i) selecting one first pixel portion;
       (ii) determining adjacent first pixel portions to the selected one first pixel portion;
       (iii) performing a first averaging of the value of the selected one first pixel portion and the determined adjacent first pixel portions;
       (iv) assigning the first average value to the selected one first pixel portion;
    performing (i) through (iv) for each of the first pixel portions in the array of pixels;
    dividing each first pixel portion into a plurality of second pixel portions;

determining a second average value including:
(a) selecting one second pixel portion;
(b) determining adjacent second pixel portions to the selected one second pixel portion;
(c) performing a second averaging based on the first average value of the selected one first pixel portion and the determined adjacent first pixel portions;
(d) assigning the second average value to the selected one second pixel portion;

performing (a) through (d) for each of the second pixel portions in the array of pixels; and outputting at least one of the determined first average value or the determined second average value;

wherein the outputted at least one of the determined first average value or the determined second average value includes a temperature;

wherein outputting at least the determined first average value or the second average value includes displaying at least one first pixel portion or at least one second pixel portion with a display device;

wherein a selected temperature range is not displayed and appears invisible on the display device.

11. The method of claim 10, wherein outputting at least one of the determine first average value or the determined second average value includes illustrating a color related to each of the first pixel portion or the second pixel portions, respectively.

12. The method of claim 10, further comprising:
dividing each second pixel portion into a plurality of third pixel portions; and
determining a third average value for each of the third pixel portions.

13. A system operable to generate hyper-spatial temperature data of a patient, comprising:
a processor system configured to execute instructions to:
determine bounding pixels of a first pixel;
divide the first pixel into a plurality of first pixel portions;
divide each of the bounding pixels into a plurality of respective bounding first pixel portions;
select at least a sub-plurality of the first pixel portions of the plurality of first pixel portions and a sub-plurality of respective bounding first pixel portions of the plurality of respective bounding first pixel portions as adjacent pixel portions to a selected one first pixel portion of the plurality of first pixel portions;
determine a value for the selected one first pixel portion based on the adjacent pixel portions;
output the determined value;
a display device configured to display the output value;
a temperature data acquisition system; and
a navigation system configured to determine a position having the determined value relative to the patient;
wherein the output determined value includes a color and the display device displays the color;
wherein the determined value includes a determined temperature and the color relates to the determined temperature;
wherein a selected temperature range is not displayed and appears invisible on the display device.

* * * * *

UNITED STATES PATENT AND TRADEMARK OFFICE
CERTIFICATE OF CORRECTION

| | | |
|---|---|---|
| PATENT NO. | : 11,615,561 B2 | Page 1 of 1 |
| APPLICATION NO. | : 17/080407 | |
| DATED | : March 28, 2023 | |
| INVENTOR(S) | : Vincelette et al. | |

It is certified that error appears in the above-identified patent and that said Letters Patent is hereby corrected as shown below:

In the Specification

Column 8, Line 15, Delete "130a "." and insert --130a"".-- therefor

Signed and Sealed this
Fifteenth Day of August, 2023

*Katherine Kelly Vidal*

Katherine Kelly Vidal
*Director of the United States Patent and Trademark Office*